United States Patent
Moroder et al.

(10) Patent No.: US 7,038,074 B2
(45) Date of Patent: May 2, 2006

(54) ARGININE MIMETICS AS FACTOR $X_A$ INHIBITORS

(75) Inventors: Luis Moroder, Martinsried (DE); Stefan Sperl, Munich (DE); Jörg Stürzebecher, Erfurt-Rhoda (DE)

(73) Assignee: Wilex AG, Munich (DE)

( * ) Notice: Subject to any disclaimer, the term of this patent is extended or adjusted under 35 U.S.C. 154(b) by 0 days.

(21) Appl. No.: 10/182,706

(22) PCT Filed: Feb. 9, 2001

(86) PCT No.: PCT/EP01/01423

§ 371 (c)(1),
(2), (4) Date: Aug. 7, 2002

(87) PCT Pub. No.: WO01/58859

PCT Pub. Date: Aug. 16, 2001

(65) Prior Publication Data

US 2003/0021773 A1    Jan. 30, 2003

(30) Foreign Application Priority Data

Feb. 9, 2000    (DE) ................. 100 05 631

(51) Int. Cl.
*C07C 229/00*    (2006.01)

(52) U.S. Cl. ............ 560/155; 560/173; 564/123; 564/148; 564/149; 564/152; 564/153

(58) Field of Classification Search ............ 564/511, 564/457, 452, 453, 225, 244, 245, 246
See application file for complete search history.

(56) References Cited

FOREIGN PATENT DOCUMENTS

| DE | 25 40 134 | 3/1976 |
|----|-----------|--------|
| EP | 0 097 630 | 1/1984 |
| EP | 0 513 675 | 11/1992 |
| EP | 513675 | * 11/1992 |
| WO | 9417035 | * 8/1994 |
| WO | WO 94 23758 | 10/1994 |

OTHER PUBLICATIONS

Sperl et al., Biol. Chem. 381 321-329.*
Journal of Enzyme Inhibition (1995), 9(1), 87-99 (Chemical Abstracts online abstract [retrieved on Nov. 18, 2005] Columbus OH, USA).*
Stefan Sperl et al.: "Urethanyl-3-Amidinophenylalanine Derivatives as Inhibitors of Factor Xa. X-Ray Crystal Structure of a Trypsin/Inhibitor Complex and Modeling Studies" Biological Chemistry, vol. 381, Apr. 2000, pp. 321-329, XP001002861.
Torsten Steinmetzer et al.: "Pept. Proc. Am. Pept. Sym. 15th; A Novel Approach for SPPS of Compounds with an Amidino Group in the C-terminal Residue Using Trityl Resins" 1999, Kluwer, Dordrecht, NL XP001002826; p. 261, col. 262.

(Continued)

*Primary Examiner*—Johann Richter
*Assistant Examiner*—Karl Puttlitz
(74) *Attorney, Agent, or Firm*—Rothwell, Figg, Ernst & Manbeck, P.C.

(57) ABSTRACT

The invention relates generally to a novel type of arginine mimetics which are inhibitors of factor $X_a$; to pharmaceutical compositions which comprise these mimetics; and to the use of these arginine mimetics for producing compositions for antithrombotic therapy.

10 Claims, 6 Drawing Sheets

OTHER PUBLICATIONS

Figure 1:
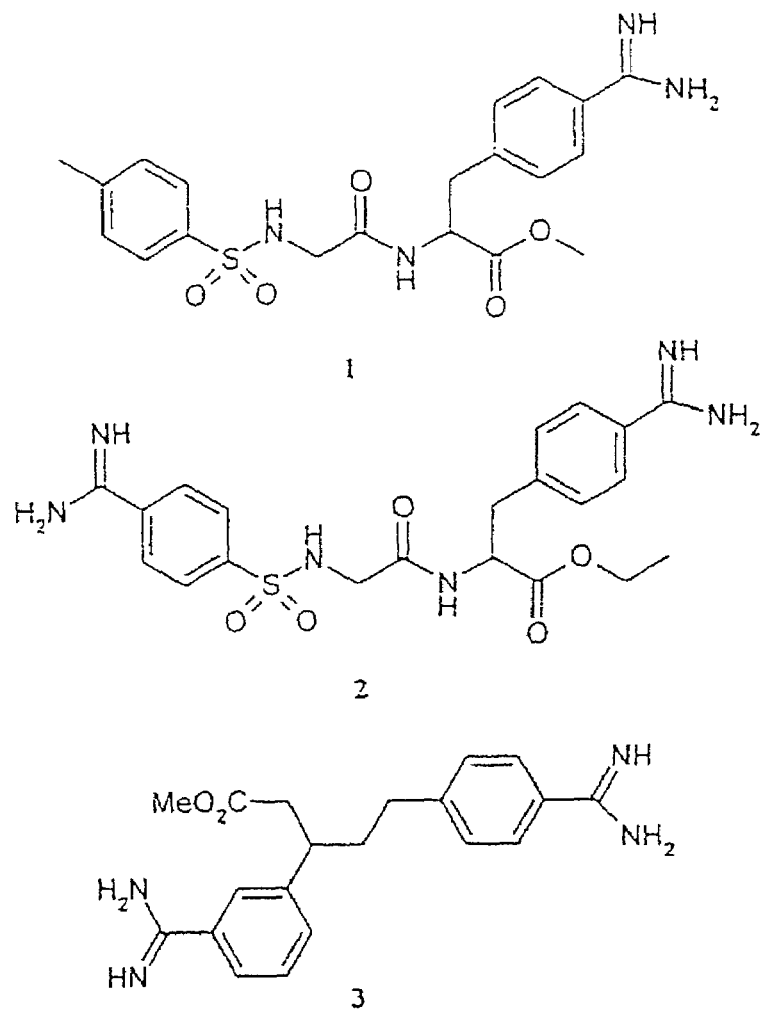

Markus Böhm et al.: "Three-Dimensional Quantitative Structure-Activity Relationship Analysis Using Comparative Molecular Field analysis and Comparative Molecular Similarity Indices Analysis to Elucidate Selectivity Differences of Inhibitors Binding to Trypsin, Thrombin, and Factor Xa" Journal of Medicinal Chemistry., vol. 42, 1999, pp. 458-477, XP002169712 American Chemical Society, Washington., US; ISSN 0022-2623; p. 464, col. 1, line 1.

B. Voigt et al.: "Synthese von N-alpha-Benzyloxcarbonyl-4-amidinophenyla laninamiden als thrombininhibitoren" Pharmazie., vol. 40, No. 5, 1985, pp. 305-306, XP002169713; Berlin DD.

J. Stürzebecher et al.: "Synthetische Inhibitoren der Serinproteasen" Pharmazie., vol. 42, No. 2, 1987, pp. 114-116, XP002169714 Veb Verlag Volk Und Gesundheit, Berlin., DD ISSN: 0031-7144 tables 1-3.

Hideaki Tsunematsu et al.: "A New beta-Naphthylamide Substrate of p-Guanidino-L-Phenylalanine for Trypsin and Related Enzymes" Journal of Biochemistry., vol. 98, No. 6, Dec. 1985, pp. 1597-1602, XP002169715 Japanese Biochemical Society, Tokyo., JP ISSN: 0021-924X; p. 1598, col. 1, line 17-line 18.

R. Alan Chrusciel et al.: "4-Acetamidophenyl Esters and 4-Acetamindoanilides of L-Arginine, p-Guanidino-L-phenylalanine, L-Lysine, N2-'D-Fructos-3-0-yl and D-Glucos-3-0-yl l acetyl-L-lysine as Potential Acrosin Inhibitors" Tetrahedron, (INCL Tetrahedron Reports), vol. 47, No. 42, 21 Oxford GB; p. 8848, line 22-line 32; table A.

Daniel A. Pearson et al.: "Thrombus Imaging Using Techneticum-99m-Labeled High-potency GPIIB/IIIa Receptor Antagonists. Chemistry and Initial Biological Studies" Journal of Medicinal Chemistry., vol. 39, No. 7, 1996, pp. 1372-1382, XP002169717; American Chemical Society, Washington, US ISSN: 0022-2623; seite 1375, Schema 5, Verbindung 28; Seite 1380, Spalte 2, Zeile 42-Zeile 63.

Yusuke Sasaki et al.: "Studies on Analgesic Oligopeptides. II. Structure-Activity Relationship among Thirty Analogs of a Cyclic Dipeptide, Cycly (-Tyr-Arg-)" Chemical and Pharmaceutical Bulletin., vol. 30, No. 12, Dec. 1982, pp. 4435-4443, XP002169718 Pharmaceutical Society of Japan, Tokyo, JP ISSN: 0022-2623; p. 4441, line 3-line 13.

* cited by examiner

| Inhibitor | Ki [µM] | | |
|---|---|---|---|
| | fXa | Thrombin | Trypsin |
| 1 | 0.84 | 3.9 | 5.6 |
| 2 | 0.50 | 41 | 4.2 |
| 3 | 0.034 | 1.2 | 0.099 |

| Compound | R¹ | R² | R³ | Ki [μM] | | | |
|---|---|---|---|---|---|---|---|
| | | | | fXa | uPA | Thrombin | Trypsin |
| (8) | (Boc) | OMe | 3-Amidino | 16 | 36 | 10 | 13 |
| (10) | (Fmoc) | OMe | 3-Amidino | 3.4 | 140 | 12 | 12 |

| Compound | Enantiomer | $K_i$ [μM] | | | | |
|---|---|---|---|---|---|---|
| | | fXa | uPA | Thrombin | Trypsin | Plasmin |
| (27) | L | 4.6 | 59 | 8.6 | 17 | 16 |
| (28) | D | 0.39/0.24* | >1000 | 1.6 | 5.7 | 8.9 |

| Compound | R | Enantiomer | $K_i$ [μM] | | | | |
|---|---|---|---|---|---|---|---|
| | | | Plasmin | uPA | Thrombin | Trypsin | fXa |
| (29) | [propyl-NH] | D | ~50 | 400 | 2.8 | 40 | 0.34 |
| (30) | [benzyl-NH] | D | 26 | >1000 | 1.3 | 4.6 | 0.22/0.21* |
| (31) | [phenethyl-NH] | D | ~39.1 | >1000 | 1.16 | 2.74 | 0.074/0.099* |

| Compound | R2 | Enantiomer | K$_i$ [μM] | | | | |
|---|---|---|---|---|---|---|---|
| | | | fXa | uPA | thrombin | trypsin | plasmin |
| (32) | | D | 0.025 | >1000 | 0.9 | 7 | 37 |

ARGININE MIMETICS AS FACTOR $X_A$ INHIBITORS

The invention relates generally to a novel type of arginine mimetics, which are inhibitors of factor $X_a$; to pharmaceutical compositions which comprise these mimetics; and to the use of these arginine mimetics for producing medicines for antithrombotic therapy.

Proteins, such as thrombin, which are involved in the blood coagulation cascade have for many years now been potential targets in the treatment of vascular diseases, with the aim of inhibiting of them and thereby avoiding thrombotic vascular occlusions or reopening thrombotically occluded blood vessels. The use of conventional anticoagulants which contain thrombin inhibitors is problematical since they increase the probability of bleeding complications (G. J. Phillipides and J. Loscalzo (1996), Coronary Artery Dis., 7, 497–507). Furthermore, directly inhibiting thrombin does not interrupt the production of thrombin from prothrombin. In this case, therefore, it is necessary to supply relatively high doses of inhibitor continuously in order to maintain an antithrombotic effect in vivo.

Consequently, in the search for novel antithrombotic medicines, inhibition of the blood coagulation factor $X_a$ became a main target for developing active compounds. Factor $X_a$ is a trypsin-like serine protease which converts the zymogen prothrombin into its active form thrombin. By inhibiting factor $X_a$, therefore, it is possible to prevent thrombin being formed while a level of thrombin activity which is required for primary hemostasis is maintained (F. Al-Obeidy and J. A. Ostrem (1998), Drug Discovery Today, 3, 223–231).

A large number of factor $X_a$ inhibitors are nowadays known. The development of a number of these factor $X_a$ inhibitors is based on conserving the structural motif Gly-Arg (with Gly being the P2 radical and Arg being the P1 radical, i.e. Gly binds in the S2 pocket and Arg binds in the S1 pocket of the factor $X_a$ protein) at the site at which the prothrombin is cleaved by factor $X_a$. In this connection, a large number of syntheses, in which a phenylalanine radical which is substituted on its phenyl ring by a basic amidino group is used as a mimetic for the Arg radical, have been described for factor $X_a$ inhibitors (J. Stürzebecher et al., (1989), Thromb. Res. 54, 245–252). It has been found that the factor $X_a$ inhibitors in this series which have thus far been most effective are derivatives of 3'-amidinophenylalanine.

Taking the guiding structure $N^\alpha$-tosylglycyl-D,L-3-amidinophenylalanine alkyl ester (Compound 1 in FIG. 1; J. Stürzebecher et al., see above) as a starting point, a large number of peptidic bisbenzamidine compounds have been developed. The most powerful factor $X_a$ inhibitor ($K_i$=0.5 µM) from this series is $N^\alpha$-4-amidinobenzenesulfonylglycyl-D,L-4-amidinophenylalanine ethyl ester (Compound 2 in FIG. 1; B. Gabriel et al., (1998), J. Med. Chem. 41, 4240–4250), which binds "inversely" to factor $X_a$: its 4'-amidinobenzenesulfonyl group lies in the S1 pocket of factor $X_a$, while the remainder of the molecule, together with the glycyl spacer, projects into the hydrophobic S3/S4 binding sites, thereby making possible additional interactions with the electronegative cavity, which is formed by the carbonyl oxygens of Lys 96, Thr. 98 and Glu 97 and its carboxylate group, behind the hydrophobic S3/S4 region.

According to the prior art, the group which is linked N-terminally to an amidinophenylalanine radical or to another arginine mimetic constitutes the P3/P4 radical of the potential factor $X_a$ inhibitor, with the N-terminally linked group preferably being bonded to the arginine mimetic by way of a glycine spacer and a sulfonamide group.

Since then, nonpeptide bisbenzamidine compounds which possess markedly improved inhibitor properties ($K_i$=34 nM), and which are characterized by a shorter distance between the two aromatic groups, have been obtained (T. P. Maduskuie et al., (1998), J. Med. Chem. 41, 53–62). On the basis of modeling analyses, it is assumed that an inhibitor 3 of this nature (see FIG. 1) extends, by means of the m-benzamidine group, into the S1 pocket, and interacts in this pocket with the Asp 189 radical, and, by means of the p-benzamidine group, into the S4 aryl-binding pocket, where it enters into cation-π interactions and hydrophobic interactions with the surrounding radicals Phe 174, Tyr 99 and Trp 215.

Against this background, an object of the invention is to provide novel inhibitors of factor $X_a$ which are highly efficient and highly specific.

In addition, an important object of the invention is to point out possibilities for using the compounds according to the invention for producing a medicine for antithrombotic therapy.

Other objects and advantages of the invention ensue from the following description.

These objects are achieved by the subject-matter of the independent claims, in particular based on the provision of the compounds according to the invention in accordance with the structural formula I.

Advantageous embodiments are described in the subclaims.

The object is achieved, according to the invention, by providing a highly efficient and highly selective factor $X_a$ inhibitor which comprises an arginine mimetic which possesses a N-terminal radical and a C-terminal radical, with the conformation of the inhibitor enabling intermolecular interactions to take place between the C-terminal radical and the S3/S4 pocket of the factor $X_a$ protein. A binding mode of this nature, in which the C-terminal radical extends into the S3/S4 binding pocket of the factor $X_a$ protein is particularly advantageous since, in the case of the factor $X_a$ inhibitor according to the invention, the C-terminal radical, in addition to the N-terminal radical, of the arginine mimetic also enters into intermolecular interactions with the factor $X_a$ protein. Consequently, the factor $X_a$ inhibitor according to the invention can be optimized both at the N-terminal radical and at the C-terminal radical, which means that it is possible to provide inhibitor strengths which are markedly superior to those of the prior art.

A binding mode of this nature is surprising since all the arginine mimetic-based factor $X_a$ inhibitors which have thus far been disclosed in the prior art bind in a substrate-like manner. In the substrate-like binding, the arginine mimetic binds in the S1 pocket while the radical which is linked N-terminally to the arginine mimetic by way of a potential P2 radical, such as a Gly spacer or the like, extends into the S3 or S4 pocket, respectively. In the case of the factor $X_a$ inhibitor according to the invention, the arginine mimetic likewise binds in the S1 pocket but, in contrast to the factor $X_a$ inhibitors known from the prior art, the radical which is bound C-terminally to the arginine mimetic, and not the radical which is bound N-terminally, extends into the S3 or S4 pocket of the factor $X_a$ protein, respectively.

Within the context of the present invention, the following terms have the following meaning unless expressly specified otherwise:

A N-terminal radical of the arginine mimetic, or a radical which is linked N-terminally to the arginine mimetic, is a radical which is bonded to the arginine mimetic by way of the $N^\alpha$ atom of the N-terminal amino group of the arginine mimetic or by way of the group in the arginine mimetic which corresponds to the amino group of the unmodified arginine.

Correspondingly, within the context of the present invention, a C-terminal radical of the arginine mimetic, or a radical which is linked C-terminally to the arginine mimetic, is understood as being a radical which is bonded to the arginine mimetic by way of the C-terminal C atom of the carboxyl group of the arginine mimetic or by way of the group in the arginine mimetic which corresponds to the carboxyl group of the unmodified arginine.

Within the context of the present invention, intermolecular interactions are all forms of van der Waals interactions, such as electrostatic interactions between charged radicals in the inhibitor and oppositely charged groups in the factor $X_a$ protein, interactions between polar groups in the inhibitor and oppositely polarized groups in the factor $X_a$ protein, and also hydrophobic interactions between nonpolar groups in the inhibitor and in the factor $X_a$ protein, and the like, and also hydrogen bonds between the inhibitor and the factor $X_a$ protein.

In connection with the present invention, an arginine mimetic is understood as being a compound which possesses the same functional characteristics as arginine or functional characteristics which are similar to those of arginine, e.g. a side chain having a positive charge at physiological pH, as is characteristic for the guanidinium group of the side chain of arginine. Thus, an arginine mimetic can be an amino acid analog of arginine, i.e. a compound in which the N-terminal amino group, the C-terminal carboxyl group and/or the side chain of arginine has been chemically modified.

Amino acid analogs in which the side chain comprises a substituted or unsubstituted, saturated or unsaturated, carbocyclic or heterocyclic radical can, in particular, be used as arginine mimetics in the present invention. While a ring of this nature is preferably a phenyl ring, it can also be a pyridine ring or a piperidine ring, or another saturated or unsaturated or aromatic, carbocyclic or heterocyclic group, with it being possible for the heteroatom(s) to be nitrogen, oxygen and/or sulfur.

Substituents of such a previously mentioned carbocyclic or heterocyclic radical are preferably basic substituents such as amidino, guanidino, amino, alkylamino, aminoalkyl, amide substituents and the like. It is furthermore also advantageously possible to use polar substituents such as halogens, e.g. chlorine, hydroxyl or alkoxy. The abovementioned carbocyclic or heterocyclic radicals can be substituted once or more than once by the abovementioned substituents, with combinations of the abovementioned substituents also being possible.

Furthermore, within the context of the present invention, the term arginine mimetics also encompasses modifications of the N-terminal amino group and of the C-terminal carbonyl group, with the proviso that these modifications exhibit the same, or essentially the same, spatial configurations as are typical for the unmodified arginine backbone. An example of such a modification is the reduction of the C-terminal carbonyl group to a $CH_2$ group.

In the present invention, it is in principle also possible to use other arginine mimetics which are known from the prior art, or which are derived therefrom, with the proviso that the arginine mimetic meets the steric requirements for a P1 substrate of the factor $X_a$ protein and the C-terminal radical of the arginine mimetic can enter into intermolecular interactions with the S3/S4 pocket of the factor $X_a$ protein.

In the present invention, the greatest preference is given to using, as the arginine mimetic, a phenylalanine analog which is substituted by a basic radical on the aromatic ring. Most preferably, the basic substituent is an amidino group at the 3 position of the aromatic ring.

When an amino acid analog, such as the above-described phenylalanine analog, is used as the arginine mimetic, the above-described, advantageous binding mode of the factor $X_a$ inhibitor according to the invention is achieved by the chirality at the $C^\alpha$ atom of the arginine mimetic, or at a corresponding chiral center of a backbone-modified arginine mimetic, being R, such that the radical which is linked C-terminally to the arginine mimetic extends into the S3/S4 pocket of the factor $X_a$ protein and can there enter into intermolecular interactions with the hydrophobic groups of the S3/S4 pocket.

When used as an arginine mimetic, a (R)-chiral amino acid analog has the additional advantage that it is more stable than (S)-chiral amino acid analogs and that the inhibitor can consequently remain active for a longer period in the body when used pharmacologically.

In a preferred embodiment of the present invention, the C-terminal radical of the arginine mimetic comprises a linker which is bonded directly to the arginine mimetic and also an optionally substituted hydrophobic group which can enter into intermolecular interactions with the hydrophobic S3/S4 pocket of the factor $X_a$ protein.

The linker is preferably of a size which is suitable for bridging the S2 pocket of the factor $X_a$ protein, i.e. its spatial configuration is preferably similar to that of the natural P2 substrate Gly.

The hydrophobic group of the C-terminal radical preferably exhibits a spatial configuration which enables the hydrophobic group to fit optimally into the S3/S4 pocket of the factor $X_a$ protein. In addition, it is advantageous if the hydrophobic group is substituted by one or more basic substituents which are configured such that it is possible for interactions to take place with negatively charged or negatively polarized groups of the factor $X_a$ protein in the neighborhood of the S3/S4 pocket. Preferred basic substituents are amidino, guanidino, amino, alkylamino, aminoalkyl and amide substituents, and the like.

The present invention relates, in particular, to compounds in accordance with the following structural formula I:

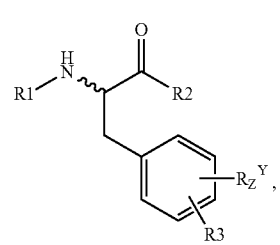

in which $R^1$ comprises a linker $L^1$, which is directly bonded to the phenylalanine analog, and a substituted or unsubstituted, saturated or unsaturated group $R^4$; $R^2$ comprises a linker $L^2$, which is bonded directly to the phenylalanine analog, and a substituted or unsubstituted, saturated or unsaturated group $R^7$; and $R^3$ is a basic substituent at the 3 or 4 position of the aromatic ring of the phenylalanine analog and the aromatic ring is optionally substituted by at least one further substituent $R^Y$, where z=0 to 4.

The linker $L^1$ is used for linking the group $R^4$ to the nitrogen atom of the phenylalanine analog of the formula I. In this connection, $L^1$ can be any group which enables such a linkage to take place. Preference is given to $L^1$ being a group which is chemically and enzymatically stable in order to prevent the compound of the formula I breaking down when being used as a pharmaceutical composition.

The linker $L^1$ can simply be a bond. In that case, $R^4$-$L^1$NH . . . is $R^4$—NH . . . Preferably, the linker $L^1$ comprises a group $R^x$ having a chain length of from 1 to 10 atoms, preferably of from 1 to 5 atoms, such as $C_1$–$C_{10}$, in particular $C_1$–$C_5$-alkyl, $C_1$–$C_{10}$-, in particular $C_1$–$C_5$-alkenyl, $C_1$–$C_{10}$-, in particular $C_1$–$C_5$-alkynyl, with this group also being able to contain heteroatoms, in particular O, S or N, in the chain, e.g. (O—$CH_2$—$CH_2$)$_n$ in which n=1 to 3. Particularly preferably, the linker $L^1$ comprises, in addition to said group $R^x$ or without said group $R^x$, a linking group which is bonded to the nitrogen as phenylalanine analog.

Particularly preferably, $R^1$ comprises a linker $L^1$ which is capable of forming hydrogen bonds. Linkers $L^1$ or linking groups which are capable of forming hydrogen bonds, or potential hydrogen acceptors or donors, which are additionally preferred because of their geometry, comprise linkers, such as —CO—, —CO—NH— or —COO—, which, together with the NH group of the phenylalanine analog, form an amide bond (in the case of —CO—), a urea bond (in the case of —CO—NH—) or a urethane bond (in the case of —COO—) An N-terminal linkage of the group $R^4$ by way of an —$SO_2$-linker is likewise possible.

Examples of preferred $R^1$ radicals are —CO—$R^4$, —CO—NH—$R^4$ or —COO$R^4$, and corresponding sulfur groups —CS—$R^4$, —CS—NH—$R^4$ or —COS$R^4$. Particularly preferably, $R^1$ is =COO$R^4$. Even more preferably, $R^1$=—CO—NH—$R^4$. The abovementioned group $R^x$ can be arranged between the linking group and the radical $R^4$. It has been found that urea derivatives ($L^1$=—CO—NH—) inhibit $FX_a$ outstandingly well and are extremely stable chemically and enzymatically, for which reason they are particularly suitable as inhibitors of $FX_a$.

However, the linker $L^1$ can also be glycine (—CO—$CH_2$—NH—) or another natural or unnatural amine acid (—CO—CHR—NH—).

The group or radical $R^4$ is preferably a hydrophobic radical. However, it can also be a hydrophilic radical or a radical which possesses a hydrophobic group which carries one or more hydrophilic substituents. $R^4$ can, for example, be a saturated or unsaturated, substituted or unsubstituted, noncyclic alkyl radical; a saturated or unsaturated, substituted or unsubstituted carbocyclic radical; or a saturated or unsaturated, substituted or unsubstituted heterocyclic radical.

$R^4$ is preferably a $C_{1-30}$-alkyl-, $C_{2-30}$-alkenyl-, $C_{2-30}$-alkynyl-, $C_{3-30}$-cycloalkyl-, $C_{5-30}$-aryl-, $C_{3-30}$-heteroaryl-, $C_{6-30}$-alkaryl- or $C_{4-30}$-alkheteroaryl radical, with these radicals being able to carry one or more substituents. $R^4$ preferably comprises at least 4 C atoms, more preferably at least 6 C atoms and preferably up to 24 C atoms, more preferably up to 18 C atoms. Suitable heteroatoms which the $R^4$ radical can contain are, for example, O, N, S and P. The radical $R^4$ can furthermore have one or more substituents. $R^4$ is preferably a noncyclic $C_1$- to $C_5$-alkyl radical which is substituted by at least one radical $R^6$, with $R^6$ being selected from $C_nH_{2n+1}$, where n=1 to 10. $R^4$ is particularly preferably t-butyl. In another preferred embodiment, $R^4$ is substituted or unsubstituted phenyl, benzyl, fluorenyl, naphthyl, —$C(CH_3)_2$—$C_6H_5$ or adamantyl. Most preferably, $R^4$=adamantyl.

Particularly preference is furthermore given to $R^4$ radicals which are larger (on the basis of the volume occupied) than is the phenyl radical.

According to the invention, the linker $L^2$ which is bonded directly to the phenylalanine analog is preferably of a size which is suitable for bridging the S2 pocket of the factor $X_a$ protein, i.e. its spatial configuration is preferably similar to that of the natural P2 substrate Gly. In this connection, the linker of $R^2$ is preferably —$OR^5$—, —NH—$R^5$—, —NH—NH—$R^5$— or —$CH_2R^5$, where $R^5$ is a substituted or unsubstituted, saturated or unsaturated, carbocyclic, heterocyclic or noncyclic alkyl radical, or can be a group $R^x$, as defined above. Particularly preferably, the linker is $L^2$=—NH—$R^5$—. However, the linker $L^2$ can also simply be a bond.

It is advantageous for a factor $X_a$ inhibitor according to the invention having the structural formula I if a hydrophobic $R^5$ radical is C-terminally linked to the phenylalanine derivative by way of an ester or amide bond, with $R^5$ particularly preferably being a substituted or unsubstituted $C_1$- to $C_5$-alkyl radical. In this connection, $R^5$ can have the formula —$(CH_2)_m$—, in which m=1 to 3. Particularly preferably, $R^5$ is =—$CH_2$—$CH_2$—. Furthermore, $R^2$ comprises a saturated or unsaturated group $R^7$ which is unsubstituted or substituted by one or more radicals $R^8$ and which can be a noncyclic radical but is, in particular, a carbocyclic radical, such as a cyclic alkyl, alkylaryl, arylalkyl or aryl radical or a heterocyclic radical which contains at least one heteroatom, such as oxygen, nitrogen and/or sulfur, with $R^8$ preferably being a basic substituent and/or a substituent which functions as a hydrogen bond donor or acceptor, and/or a halogen.

$R^7$ is preferably a $C_{1-30}$-alkyl, $C_{2-30}$-alkenyl, $C_{2-30}$-alkynyl, $C_{3-30}$-cycloalkyl, $C_{5-30}$-aryl, $C_{3-30}$-heteroaryl, $C_{6}$–$C_{30}$-alkaryl or $C_{4-30}$-alkheteroaryl radical, with these radicals being able to carry one or more substituents. $R^7$ preferably comprises at least 4 C atoms, more preferably at least 6 C atoms and preferably up to 24 C atoms, more preferably up to 18 C atoms. Suitable heteroatoms which the $R^7$ radical can contain are, for example, O, N, S and P. The $R^7$ radical can additionally possess one or more substituents.

In particular, R can be a phenyl, piperidine, pyrrol, furan, thiophene, pyridine, naphthalene, anthracene or indole radical which is unsubstituted or substituted by one or more $R^8$ radicals. Other aromatic radicals, including fused aromatic or heteroaromatic radicals, are likewise conceivable.

$R^8$ is preferably a radical which is a positively charged radical under physiological conditions, e.g. a pH of approx. 6.5–7.5.

Particularly preferably, $R^8$ is an amidino, guanidino, amino, ester, alkylamino, aminoalkyl, cyano, amide or hydroxyl radical, or the like.

Particularly advantageously for the use of the compounds according to the invention having the structural formula I as factor $X_q$ inhibitors, a radical —NH—$CHR^9$—COO—$(CH_2)_mR^7$, in which m=1 to 5, $R^7$ is as defined above and $R^9$ is a derivatized or nonderivatized side chain of a natural amino acid, and which can readily be produced synthetically by esterifying a natural or unnatural amino acid, can be used as the radical $R^2$.

In the present invention, $R^3$ is preferably an amidino, guanidino, amino, alkylamino, aminoalkyl or amide radical, or the like, particularly preferably an amidino radical. The aromatic ring of the phenylalanine radical is substituted at the 3 or/and 4 position, preferably at the 3 position, by the radical $R^3$, e.g. an amidino radical.

Furthermore, the ring can also advantageously be additionally substituted by one or more substituents $R^Y$, where z=0 to 4. Preference is given to polar substituents, such as halogen, e.g. fluorine, chlorine, bromine, iodine, hydroxyl or alkoxy and/or basic substituents.

$R^Y$ can preferably, in each case independently at each occurrence, be a halogen, e.g. fluorine, chlorine, bromine, iodine, —OH, —$NH_2$, -formyl, -acetyl, —OMe (Me=methyl), —OEt (Et=ethyl), NHMe, —NHEt, SH, SEt, SMe, $NMe_2$, —$CH_3$, —$CH_2OH$, —$CH_2$—$CH_3$, —NH—OH, —COOH, —COOMe, CN, $NO_2$ or —$CH_2CH_3$.

The groups mentioned for the substituent $R^y$ are also preferred substituents for the other substituted groups mentioned herein (e.g. in the case of $R^4$, $R^5$ and $R^7$), unless explicitly indicated otherwise.

Surprisingly, it has been found that it is advantageous for inhibiting factor $X_a$ with a compound according to the invention of the structural formula (I) if the phenylalanine analog is (R) chiral, because the C-terminal radical is then able to enter into intermolecular interactions with the S3/S4 pocket of the factor $X_a$ protein. Preference is therefore given to the abovementioned compounds being in the (R) conformation. However, the invention also encompasses the compounds in the (S) conformation, and also mixtures of (R) and (S) enantiomers.

A very powerful inhibitory effect on factor $X_a$ was achieved using the compound according to the invention N-1-adamantyloxycarbonyl-D-3-amidinophenylalanine-(2-phenyl)-1-ethylamide.

An even more powerful inhibitory effect on factor $X_a$ was observed in the case of the compound according to the invention N-(1-adamantylaminocarbonyl)-D-3-amidinophenylalanine-(2-phenyl)-1-ethylamide.

The compound according to the invention can be present in free form or as a pharmaceutically acceptable salt, for example as a hydrochloride.

Figure 2:
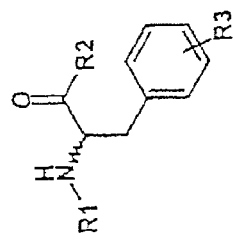
Figure 3:
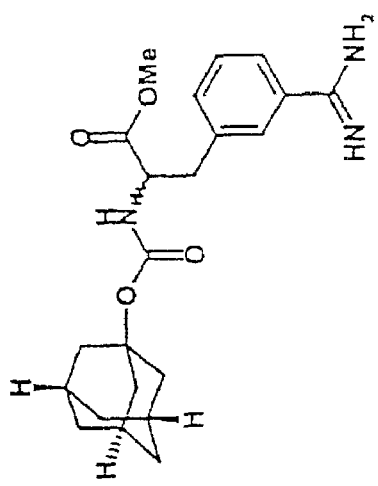
Figure 4:
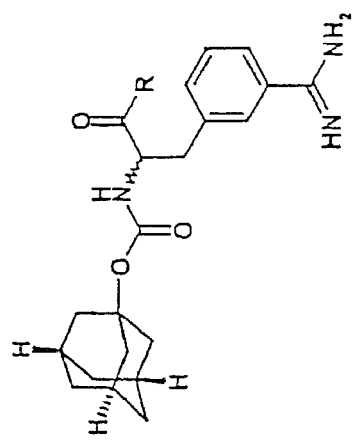

In that which follows, the present invention is illustrated using representative compounds according to the invention. FIGS. 2 to 4 list their inhibitory strengths toward factor $X_a$ and, by comparison, toward uPA, thrombin and trypsin.

The preference of factor $X_a$ for 3-amidinophenylalanine derivatives as compared with 4-amidinophenylalanine derivatives is in agreement with previous publications (Maduskuie et al., see above), although a preference for the 4-amidino group was observed in the case of the inverse binding of the bisbenzamidine compound 2 (B. Gabriel et al., see above). Interestingly, the 4-guanidinoderivative 26 in no way meets the steric requirements for a P1 radical for this enzyme since a dramatic loss in inhibitory activity is observed as compared with compound 19. This also applies to the other enzymes investigated, i.e. uPA, thrombin and trypsin.

Comparison of the racemic compound 15, as a free acid at the C terminus, with the racemic compound 17, as a C-terminal amide derivative, does not show any important differences, an observation which is in agreement with the crystal structure of des-Gla-factor $X_a$-complexed DX-9065a, in which the free carboxylate group extends into the surrounding solvent (H. Brandstetter et al. (1996), J. Biol. Chem. 271, 29988–29992). In a similar way, it was observed, in the prior art, that the inhibition of factor $X_a$ is not affected when the compound 2 is present as the ester derivative instead of having a free carboxyl (Gabriel et al., see above). In view of these results, the significantly increased inhibitory effect of compound 11, i.e. the C-terminal methyl ester derivative, as compared with that of compound 15, having the free C-terminal carboxyl group, is extremely surprising. Evidently, the nature of the bond differs from that of the Daiichi inhibitor DX-9065a (Brandstetter et al., see above) or from that of compound 1 (M. Renatus et al. (1998), J. Med. Chem. 41, 5445 to 5456), in that the ester group is involved in a new type of interaction in the vicinity of the S1 binding site.

The advantageous effect, which is described in the previous paragraph, on the inhibitory action is augmented when, for example, use is made of a C-terminal ester or a C-terminal amide derivative which comprises a hydrophobic group and a linker which is of a suitable size for bridging the S2 pocket of the factor $X_a$ protein, i.e. its spatial configuration is similar to that of the natural P2 substrate Gly. This is illustrated by the compounds according to the invention 29 to 31 (see FIG. 4). Thus, in the case of the strongest inhibitor 31, the group —NH—$CH_2$—$CH_2$— corresponds to the previously described linker in that it exhibits virtually the same spatial extent as does a Gly radical —NH—$CH_2$—CO—. The preferred hydrophobic group is a substituted or unsubstituted aryl or alkylaryl group, as previously described, in order to achieve optimal intermolecular interactions with the hydrophobic S3/S4 pocket of the factor $X_a$ protein, and consequently a powerful inhibitory effect.

The effect of the chirality of the 3-amidinophenylalanine derivative on the inhibition of factor $X_a$ is depicted using as an example a preferred embodiment of the present invention, i.e. the racemic compound 11. The $K_i$ values of the L-(compound 27) and of the D-enantiomer (compound 28) are listed in Table 3. It is not possible to ascertain any clear preference between the L-(compound 27) and D-enantiomer (compound 28) by carrying out a crystal structure analysis of the known trypsin/11 complex and by carrying out modeling studies for trypsin and factor $X_a$ based on this crystal structure. This is confirmed by the $K_i$ values of trypsin, since trypsin recognizes both enantiomers 27 and 28 with almost identical affinity, and only with a slight preference for the D-enantiomer. On the other hand, when inhibiting factor $X_a$, the D-enantiomer 28, with a $K_i$=0.39 µM, surprisingly exhibits an activity which is about 10 times greater than that of the L-enantiomer 27. Whereas the affinity of this type of inhibitor for trypsin and thrombin is only marginally influenced by the chirality of the 3-amidinophenylalanine radical, uPA is, on the other hand, only capable of recognizing the L-enantiomer. This is, therefore, the first report of the inhibitory strength for factor $X_a$ being dependent on the chirality of the arginine mimetic employed and, in particular, the first report of a R-chiral arginine mimetic being an effective inhibitor of factor $X_a$.

This preference of factor $X_a$ for the (R) chirality of the arginine mimetic is an essential feature of the present invention which it was not possible to expect on the basis of the known investigations. The fact that the chirality at this position has an influence on selectivity with regard to the inhibition of uPA, trypsin and thrombin, since uPA is selective for the (S) chirality whereas both trypsin and thrombin recognize both isomers with comparable affinities, is also surprising.

Modeling studies carried out on the complex of factor $X_a$ and compound 11, and based on the known crystal structure of factor $X_a$ (K. Padmanabhan et al. (1993), J. Mol. Biol. 232, 947–966), indicate that the bonding is of the following nature: the benzamidino group of N-1-adamantyloxycarbonyl-D-3-amidinophenylalanine methyl ester (28) lies in the S1 pocket while the adamantyl group is located in a slight recess surrounded by the side chains of Trp 215, Glu 217 and Phe 174 south of the substrate S3/S4 aryl binding site. In this type of binding, the C-terminal ester group points in the direction of the S3/S4 substrate binding pocket, with this being able to explain the preference for the (R) chirality. It can be presumed that a similar binding mechanism also operates in the case of the particularly preferred compounds according to the invention, 29 to 31.

A comparison of hydrophobic head groups which are N-terminally linked to the 3-amidinophenylalanine, such as of the tert-butyl group (compound 8), of the 9-fluorenylmethyl group (compound 10), of the 1-adamantyl group (compound 11) and of the benzyl group (compound 4), clearly shows that nonplanar and nonaromatic groups are most suitable. Thus, the compound 11, having the 1-adamantyl group, leads to a submicromolar inhibition of factor $X_a$ and, at the same time to remarkable selectivity vis-à-vis uPA, thrombin and trypsin.

While, with the exception of dramatic effects on the inhibition of uPA, the replacement of the N-terminal urethane group, as a potential water bond acceptor in compound 11, with the related urea group (compound 12) evidently does not have any effect on the hydrogen bond network in this segment of the protease/inhibitor complex, it leads to a desirable stability towards acids, for example stomach acids.

With regard to selectivity, the most marked effects are achieved by means of a free carboxyl group at the C terminus, which group evidently impairs the interactions with uPA, thrombin and trypsin at their active sites in a specific manner. In a similar way, a 4-guanidino group impairs the inhibition not only of factor $X_a$ but also of other trypsin-like enzymes which have been investigated.

The compounds according to the invention are synthesized by means of a process which comprises the following steps:
  a) adding $R^4$—NCO, $R^4$—NCS, X—CO—$R^4$, X—$SO_2$—$R^4$, X—CO—NH—$R^4$ or X—$COOR^4$ to D- or L-phenylalanine which possesses the basic substituent $R^3$, or a precursor of $R^3$, at the 3 or 4 position;
  b) where appropriate converting the precursor of $R^3$ into the substituent $R^3$;
  c) where appropriate adding $YR^5$ to the reaction product from step b).

In this connection, X can be Cl or an active ester. In the same way, the abovementioned compounds which contain the $R^4$ radical can be added, if possible, in the form of their respective acid anhydrides.

The N derivatives of the racemic 3- and 4-amidinophenylalanine are obtained from the respective 3- and 4-cyano compounds, followed by their conversion into the related amidino derivatives, or by direct derivatization of the amidinophenylalanine. Owing to side reactions which arise as a result of the unprotected amidino group, and owing to difficulties in purifying the hydrophilic amidino compounds, preference is given to reaction sequences in which the amidino function is generated in conclusion. For converting the cyanophenylalanine derivatives into the corresponding amidino compounds, the cyano group can be converted into the amidino radical by adding hydroxylamine hydrochloride and subsequently performing catalytic hydrogenation. However, other modifications of the two step reaction for synthesizing N-benzyloxycarbonylamidinophenylalanine piperidide, which have been reported by Stüber et al. (Stüber et al. (1998), Peptide Res. 8, 78–85), are also possible.

When $R^2=OR^5$, the C derivatives of the racemic 3- and 4-amidinophenylalanine can be obtained by adding the corresponding alcohol, where appropriate in the presence of acid or DCC (dicyclohexylcarbodiimide). When $R^2=NHR^5$, it is possible to use the corresponding amine or a corresponding amino acid, where appropriate in the presence of condensing reagents which are customarily used in peptide synthesis. The examples of such condensing reagents are HOBT and TBTU. An important aspect of the present invention is the use of the compounds according to the invention for producing a composition for anticoagulatory therapy. In connection with the present invention, anticoagulatory therapy is understood as being the treatment of vascular diseases in order to avoid thrombotic vascular occlusions (antithrombotic therapy). Therapies of this nature comprise the prophylaxis and therapy of the venous thromboses and lung embolisms and the antithrombotic therapy of arterial thromboses and embolisms, including coronary heart diseases such as angina pectoris or acute myocardial infarction, cerebrovascular blood flow disturbances, such as transient ischaemic attacks and cerebral infarctions, and peripheral arterial occlusion diseases. In addition, the compounds according to the invention can be used for hemorheologic therapy, i.e. for improving the flowability of the blood.

The compounds according to the invention of the structural formula I can also be conceived as being suitable inhibitors of other serine proteases, in particular of human thrombin, plasma kallikrein and plasmin. In connection with such an inhibitory effect, the compounds according to the invention can be used for preventing or treating physiological reactions, blood coagulation and inflammatory processes which are catalyzed by the abovementioned class of enzymes.

The present invention furthermore relates to a pharmaceutical composition which, where appropriate, comprises a pharmaceutically acceptable excipient and at least one of the compounds according to the invention. Preference is given to the pharmaceutical composition comprising a therapeutically effective quantity of the compounds according to the invention. A "therapeutically effective quantity" is understood as being a quantity of the compounds according to the invention having the structural formula I which, when administered on its own to a mammal, or administered to a mammal in combination with an additional therapeutic agent, exhibits therapeutic activity and is, in particular, active antithrombotically or as an antitumor agent.

Within the context of the present invention, "administration in combination" or "combination therapy" means that the compounds according to the invention of the formula I and one or more additional therapeutic compositions are administered alongside each other to the mammal to be treated. When administration takes place in combination, each component can either be administered at the same time or consecutively at different times in any sequence. Consequently, each component can be administered separately but sufficiently close to each other chronologically to ensure that they provide the desired therapeutic effect. Other anticoagulants (or coagulation inhibiting agents) which can be used in combination with the compounds according to the invention include warfarin and heparin and other factor $X_a$ inhibitors which have been described in the prior art.

The administration of the compounds according to the invention in combination with such additional therapeutic compositions can afford an advantage as compared with the respective use of the compounds and compositions on their own by, for example, making it possible to use lower doses in each case, thereby minimizing any possible side effects.

The compounds according to the invention are suitable, in particular, for treatment or prophylactic use in association with diseases which are associated with a pathological expression or overexpression of factor $X_a$ and/or involve an increase in factor $X_a$ proteolytic activity which can in turn be responsible for tumor growth-promoting and metastasis-promoting fibrin depositions.

Thus, the compounds according to the invention are able to efficiently inhibit and/or prevent the growth and/or spread of malignant tumors and the metastasis of tumors. The invention therefore also relates to the use of the compounds according to the invention for producing an antitumor agent. In this connection, the factor $X_a$ inhibitors according to the invention can, where appropriate, be formulated together with suitable pharmaceutical auxiliary substances or carrier substances for the purpose of producing drugs. It is furthermore possible, where appropriate, to use the factor $X_a$ inhibitors together with other tumor agents or other active compounds or with other types of treatment, for example in combination with irradiation or surgical interventions. Tumors which exhibit factor $X_a$ activity, and which are suitable for being treated with the compounds according to the invention, are, in particular, lung, bladder, liver and ovarian carcinomas, and also malignant melanomas and neuroblastomas.

The compounds according to the invention already inhibit FXa at low concentrations. For example, the compound 31 which is presented herein inhibits with an inhibitor constant Ki=0.074 μM. Whereas the desired FXa inhibition already takes place at such low concentrations, blood coagulation (according to the APPT test) is only affected at substantially higher concentrations of the compounds according to the invention. As a result, the compounds according to the invention can be used selectively for inhibiting FXa without blood coagulation being affected at the same time. In this way, it is possible to use the compounds according to the invention for controlling cancer (which control is connected with the inhibition of FXa) while being able to avoid side-effects, such as bleeding (which is connected to blood coagulation). This constitutes a fundamental advantage of the compounds according to the invention as compared with other FXa inhibitors, such as the known DX-9065a (Kakkar et al., J. Clinical Pathology—Clinical Molecular Pathology Edition 48(5):M288–M290, 1995; Gouinthibault et al., British Journal of Haematology 90(3): 669–680; Nakata et al., Cancer Letters 122(1–2): 127–133, 1998; Yoshida et al., Fibrinolysis & Proteolysis, 11(3): 147–154, 1997; Barendsz-janson et al., Tumor Biology, 19(2): 104–112, 1998; Donnelly et al., Thrombosis & Haemostasis, 79(5): 1041–1047, 1998; Fielding et al., Blood, 91(5): 1802–1809, 1998; Tanabe et al., Thrombosis Research, 96(2): 135–143, 1999).

The pharmaceutical composition can be administered to human and animals in all known ways, for example topically, orally, rectally or parenterally, for example subcutaneously or intravenously. In addition, it can also be administered in the form of tablets, sugar-coated tablets, capsules, pellets, suppositories, solutions or transdermal systems, such as plasters.

The compounds according to the invention can also be used as standard or reference compounds, for example as a quality standard or control in tests or assays which include the inhibition of factor $X_a$. These compounds can be provided in a commercial kit, for example for use in pharmaceutical research encompassing factor $X_a$.

The compounds according to the invention can also be used in diagnostic assays which include factor $X_a$.

The compounds according to the invention can be administered in oral dosage forms such as tablets, capsules, pills, powders, granules, elixirs, tinctures, suspensions, syrups and emulsions. They can also be administered intravenously, intraperitoneally, subcutaneously or intramuscularly, in each case using dosage forms which are well known to the skilled person. While they can be administered on their own, preference is given to administering them together with a pharmaceutical excipient which is selected on the basis of the chosen route of administration and customary pharmaceutical procedures.

The dose of the compounds according to the invention will naturally depend on a variety of known factors, such as the pharmacodynamic characteristics of the particular composition and its nature and the route of administration; and on the species, the age, the sex, the health, the medical condition and the weight of the recipient, and other known factors. A skilled person is able, without further instruction, to determine the quantity of the compound according to the invention which is effective for producing a composition for antithrombotic therapy.

In general, when being used to achieve the abovementioned effects, the daily oral dose of the respective active constituents will be in the range of about 0.001 to 1 000 mg/kg of body weight, preferably of from about 0.01 to 100 mg/kg of body weight, per day and, most preferably, from about 1.0 to 20 mg/kg per day. For intravenous administration, the doses which are most preferred are in a range from about 1 to about 10 mg/kg/min during an infusion at a constant rate. The compounds according to the invention can be administered in a single daily dose or subdivided into doses which are given 2, 3 or 4 times daily.

The compounds according to the invention can also be administered in intranasal form or administered transdermally.

The compounds according to the invention are typically suitably selected in admixture with suitable pharmaceutical diluents, excipients or vehicles (which are jointly termed pharmaceutical vehicles in that which follows), with regard to the intended form of administration and in agreement with conventional pharmaceutical procedures.

Examples, in the case of oral administration in the form of a tablet or capsule, the active compound component, in the form of the compound according to the invention, can be combined with an oral, nontoxic, pharmaceutically acceptable, inert vehicle such as lactose, starch, sucrose, glucose, methyl cellulose, magnesium stearate, dicalcium phosphate, calcium sulfate, mannitol, sorbitol and the like. For oral administration in liquid form, oral active compound components can be combined with any oral, nontoxic, pharmaceutically acceptable inert vehicles such as ethanol, glycerol, water and the like.

Furthermore, if necessary or desired, it is also possible to use suitable binders, lubricants, disintegrants and dyes in the pharmaceutical composition. Suitable binders include starch, gelatin, natural sugars such as glucose or beta-lactose, natural and synthetic rubbers, carboxymethyl cellulose, polyethylene glycol, waxes and the like. Lubricants which are used in these dose forms include sodium oleate, sodium stearate, magnesium stearate, sodium benzoate, sodium acetate, sodium chloride and the like. The disintegrants comprise, inter alia, starch, methyl cellulose, agar, bentonite and the like.

The compounds according to the invention can also be administered in the form of liposomal transport systems. Liposomes can be formed from a large number of phospholipids, such as cholesterol, stearylamine or phosphatidylcholins.

The compounds according to the invention can also be linked to soluble polymers acting as active compound vehicles. These polymers include polyvinylpyrrolidone, pyran copolymer, polyhydroxypropylmethacrylamide phenol, polyhydroxyethylaspartamide phenol or polyethylene oxide polylysine which is substituted by palmitoyl radicals. Furthermore, the compounds according to the invention can be coupled to a number of biodegradable polymers which are useful for achieving controlled release of an active compound, for example to polyglycolic acid, polylactic acid, copolymers of polyglycolic acid and polylactic acid, poly-epsiloncaprolactone, polyhydroxybutyric acid, polyorthoesters, polyacetals and the like.

Lipid dosage forms for oral administration can comprise dyes or flavorings for the purpose of increasing patient acceptance.

In general, water, a suitable oil, salt solutions, aqueous dextrose (glucose) and related sugar solutions, and glycols, such as propylene glycol or polyethylene glycols, are suitable vehicles for parenteral solutions. Solutions for parenteral administration preferably contain a water-soluble salt of the active constituent, suitable stabilizers and, if necessary, buffering substances. Antioxidants, such as sodium disulfite, sodium sulfite or ascorbic acid, either alone or in combination, are suitable stabilizers.

Other suitable pharmaceutical vehicles are described in "Remington's Pharmaceutical Sciences", Mack Publishing Company, which is a standard reference work in this area.

The compounds according to the invention can also be employed as lead substances. They can, in particular, be used for developing or finding other effective factor $X_a$ inhibitors, for example using appropriate algorithms, which may, where appropriate, be computer-assisted. When employed as lead substances, the compounds according to the invention can be used, in particular, for developing novel antithrombotic and antitumor agents.

The following examples serve to explain the invention without restricting it in any way.

EXAMPLES

All the solvents and reagents which are used in the following examples were of the highest commercially available quality and, if required, were further purified and dried using standard methods. Analytical HPLC was carried out on ET 125/4 Nucleosil 100/$C_8$ columns (Macherey-Nagel, Düren, Germany) using a linear gradient of MeCN/2% $H_3PO_4$ of 5:95 (A) to 80:20 (B) in 12 minutes. ESI-MS spectra were recorded on a Perkin Elmer API 165 mass spectrometer (Perkin Elmer, Langen, Germany). TLC was carried out on silica gel 60 plates using the following solvent systems: (A) $CHCl_3$/MeOH/AcOH, 40:10:2; (B) $CHCl_3$/MeOH/AcOH, 20:20:1; (C) AcOEt/n-BuOH/$H_2O$/AcOH, 10:6:2:2; (D) $CHCl_3$/MeOH/AcOH, 190:10:2; (E) $CHCl_3$/MeOH/$NH_3$, 20:20:9; (F) $CHCl_3$/MeOH/AcOH, 10:20:1; (G) n-hexane/AcOEt/AcOH, 49:49:2.

The synthesis, and inhibitor constants, of the compounds 1 and 4 are taken from the prior art (B. Gabriel (1998), Doctoral Thesis, Technische Universität München [Munich Technical University]). N,N'-Dibenzyloxycarbonyl-N''-trifylguanidine was synthesized in accordance with Feichtinger et al. (J. Org. Chem. 63, 3804–3805, 1998). 4-Nitrophenylalanine was obtained from Bachem (Heidelberg, Germany). D,L-3-Cyanophenylalanine and D,L-4-cyanophenylalanine were obtained from Sennchemicals (Dielsdorf, Switzerland), while Boc-D-3-cyanophenylalanine and Boc-L-3-cyanophenylalanine were obtained from Syntetech (Albany, Oreg., USA). The two latter compounds were $N^\alpha$-deprotected in 95% TFA (trifluoroacetic acid).

Example 1

Synthesis of N-tert-butyloxycarbonyl-D,L-3-cyanophenylalanine (5)

$(Boc)_2O$ (5.74 g; 26.29 mmol) in dioxane (5 ml) was added to a stirred solution of D,L-(3-cyano)phenylalanine (5 g; 26.29 mmol) in dioxane (25 ml) and 1 M NaOH (26.3 ml). After one hour, the solution was evaporated and the residue was partitioned between AcOEt and 5% aqueous $KHSO_4$ solution. The aqueous phase was extracted three times with AcOEt and the combined organic phases were dried (over $Na_2SO_4$) and evaporated, resulting in a pale yellow oil, which crystallized at 4° C.

Yield: 6.9 g (91%); TLC (solvent system B): $R_f$ 0.77; HPLC: $t_R$ 8.2 min; MS m/z 291.0 (M+H)$^+$, calculated $M_r$=290.1.

Example 2

Synthesis of N-tert-butyloxycarbonyl-D,L-3-hydroxyamidinophenylalanine (6)

A solution of compound 5 (1 g; 3.44 mmol), hydroxylamine hydrochloride (359 mg; 5.17 mmol) and KOH (483 mg; 8.6 mmol) in EtOH (50 ml) was boiled under reflux overnight. Insoluble KCl was filtered off and the solution was evaporated and the residue was dissolved in water (30 ml) and acidified to pH 2.5 with 1 M HCl. The solution was washed twice with AcOEt (20 ml) and the product was subsequently extracted five times with water-saturated n-BuOH. The combined n-BuOH layers were evaporated.

Yield: 870 mg (78%) of white foam; TLC (solvent system C): $R_f$ 0.62; HPLC: $t_R$ 5.3 min; MS m/z=324.0 (M+H)$^+$, calculated $M_r$=323.2.

Example 3

Synthesis of N-tert-butyloxycarbonyl-D,L-3-amidinophenylalanine hydrochloride (7)

The compound 6 (870 mg; 2.69 mmol) was hydrogenated in water (50 ml) over 10% Pd/C at 50° C. for a period of 5 h. The catalyst was filtered off and the solution was evaporated to dryness in the added presence of 1 M HCl (2.7 ml).

Yield: 710 mg (77%); TLC (solvent system C): $R_f$ 0.18; HPLC: $t_R$ 5.4 min; MS m/z=308.4 (M+H)$^+$, calculated $M_r$=307.2.

Example 4

Synthesis of N-tert-butyloxycarbonyl-D,L-3-amidinophenylalanine methyl ester hydrochloride (8)

A solution of 7 in MeOH (5 ml) was acidified down to pH 2 with 6 M HCl and stirred at room temperature for 24 h. The solution was evaporated down to dryness.

Yield: quantitative; TLC (solvent system C): $R_f$ 0.41; HPLC: $t_r$ 5.9 min; MS m/z=322.4 (M+H)$^+$, calculated $M_r$=321.2.

Example 5

Synthesis of D,L-3-amidinophenylalanine methyl ester dihydrochloride (9)

A solution of 8 (230 mg; 0.64 mmol) in 6 M HCl in dioxane (5 ml) was stirred at room temperature. After 1 h, the solution was evaporated down to dryness.

Yield: quantitative; TLC (solvent system B): $R_f$ 0.10; MS m/z=222.2 (M+H)$^+$, calculated $M_r$=221.1.

Example 6

Synthesis of N-9-fluorenylmethyloxycarbonyl-D,L-3-amidinophenylalanine methyl ester hydrochloride (10)

Fmoc-Cl (9-fluorenylmethoxycarbonyl chloride, 44 mg; 0.17 mmol) and TEA (triethylamine, 24 µl; 0.17 mmol) were added to a solution of compound 9 (50 mg; 0.17 mmol) in DMF (500 µl). After 30 min at room temperature, TEA (12 µl) was added in order to complete the reaction. After 3 h, the solvent was evaporated and the residue was dissolved in water. After acidifying down to pH 3 with 1 M HCl, the product was collected by centrifugation and precipitated once again from AcOEt/diisopropyl ether.

Yield: 60 mg (73%); TLC (solvent system A): $R_f$ 0.58; HPLC: $t_R$ 8.0 min; MS: m/z=444.0 (M+H)$^+$, calculated $M_r$=443.2.

Example 7

Synthesis of N-1-adamantyloxycarbonyl-D,L-3-amidinophenylalanine methyl ester hydrochloride (11)

Compound 11 was prepared essentially as described for compound 10 using Adoc-F (1-adamantyloxycarbonyl fluoride) and was reprecipitated from AcOEt/diisopropyl ether.

Yield: 86%; TLC (solvent system A): $R_f$ 0.55; HPLC: $t_R$ 7.6 min; MS: m/z=400.4 (M+H)$^+$, calculated $M_r$=399.2.

Example 8

Synthesis of N-1-adamantylaminocarbonyl-D,L-3-amidinophenylalanine methyl ester hydrochloride (12)

Compound 9 (46 mg, 0.156 mmol) was reacted for 3 h in DMF (500 μl) containing 1-adamantyl isocyanate (27.7 mg; 0.156 mmol) and TEA (22 μl, 0.156 mmol). After the solvent had been evaporated, the residue was crystallized from isopropanol/diisopropyl ether.

Yield: 55 mg (81%); HPLC: $t_R$ 8.7 min; MS m/z=399.4 (M+H)$^+$, calculated $M_r$=398.2.

Example 9

Synthesis of N-1-adamantyloxycarbonyl-D,L-3-cyanophenylalanine (13)

A solution of D,L-(3-cyano)phenylalanine (2 g; 10.5 mmol), Adoc-F (2.08 g; 10.5 mmol) and 2 M NaOH (7.8 ml; 15.6 mmol) in dioxane (50 ml) was stirred at room temperature for 3 h. The residue was partitioned between AcOEt and 5% aqueous KHSO$_4$ solution. The aqueous phase was extracted three times with AcOEt and the combined organic phases were washed with salt solution, dried (over Na$_2$SO$_4$) and evaporated. The resulting yellowish oil was treated with diethyl ether and evaporated down to a white foam.

Yield: 3.7 g (96%); HPLC: $t_R$ 8.7 min; TLC (solvent system B): $R_f$ 0.72; MS m/z=369.5 (M+H)$^+$, calculated $M_r$=368.2.

Example 10

Synthesis of N-1-adamantyloxycarbonyl-D,L-3-hydroxyamidinophenylalanine hydrochloride (14)

Compound 13 (3.7 g; 10 mmol) was reacted with hydroxylamine hydrochloride and worked up as described for compound 6.

Yield: 3.9 g (97%); HPLC: $t_R$ 9.1 min; TLC (solvent system B): $R_f$ 0.66; MS m/z=402.4 (M+H)$^+$, calculated $M_r$=401.2.

Example 11

Synthesis of N-1-adamantyloxylcarbonyl-D,L-3-amidinophenylalanine hydrochloride (15)

The catalytic reduction of compound 13 (3.9 g; 9.7 mmol) was carried out as described for compound 7.

Yield: 3.5 g (86%); HPLC: $t_R$ 9.4 min; MS: m/z=386.4 (M+H)$^+$, calculated $M_r$=385.2.

Example 12

Synthesis of N-1-adamantyloxycarbonyl-D,L-3-cyanophenylalanine piperidide (16)

SOCl$_2$ (120 μl; 1.63 mmol) was added dropwise, at 0° C. and while stirring vigorously, to a solution of compound 13 (300 mg; 0.814 mmol) and piperidine (480 μl; 4.88 mmol) in methylene chloride (5 ml). After the mixture had been allowed to warm up to room temperature, and after 2 h, the reaction mixture was diluted with methylene chloride and washed with 5% aqueous NaHCO$_3$, 5% aqueous KHSO$_4$ solution, water and salt solution, and dried (over Na$_2$SO$_4$). The solution was brought to dryness.

Yield: 240 mg (68%); TLC (solvent system D): $R_f$ 0.76; MS m/z=436.2 (M+H)$^+$, calculated $M_r$=435.3.

Example 13

Synthesis of N-1-adamantyloxycarbonyl-D,L-3-amidinophenylalanine piperidide hydrochloride (17)

The reaction of compound 16 (240 mg; 0.55 mmol) with hydroxylamine hydrochloride, and the following catalytic reduction to give the compound 17, were carried out as described for compounds 6 and 7.

Yield: 84 mg (31% over the two steps); HPLC: $t_R$ 10.0 min; MS: m/z=453.4 (M+H)$^+$, calculated $M_r$=452.3.

Example 14

Synthesis of N-tert-butyloxycarbonyl-D,L-(4-amidino)phenylalanine hydrochloride (18)

Compound 18 was synthesized starting from D,L-(4-cyano)phenylalanine, as described for the 3-substituted phenylalanine 7.

Yield: 57% (over 3 steps); HPLC: $t_R$ 5.2 min; MS m/z=308.4 (M+H)$^+$, calculated $M_r$=307.2.

Example 15

Synthesis of D,L-4-amidinophenylalanine dihydrochloride (19)

The deprotection of compound 18 (625 mg; 2.037 mmol) was carried out in 6 M HCl in dioxane as described for compound 9.

Yield: 540 mg (95%); TLC (solvent system E): $R_f$ 0.23; MS: m/z=208.3 (M+H)$^+$, calculated $M_r$=207.2.

Example 16

Synthesis of D,L-4-amidinophenylalanine methyl ester dihydrochloride (20)

SOCL$_2$ (180 µl; 2.47 mmol) was added dropwise, at −70° C. and while stirring vigorously, to a solution of compound 17 (230 mg; 0.824 mmol) in MeOH (2 ml). The reaction mixture was allowed to warm to room temperature and was stirred for 18 h. The solvent was evaporated and the product was crystallized from EtOH/diethyl ether.

Yield: 182 mg (75%); TLC (solvent system E): R$_f$ 0.54; MS: m/z=222.4 (M+H)$^+$, calculated M$_r$=221.1.

Example 17

Synthesis of N-1-adamantyloxycarbonyl-D,L-4-amidinophenylalanine methyl ester hydrochloride (21)

Compound 21 was prepared from compound 20 using Adoc-F as described for compound 10.

Yield: 32 mg (43%); HPLC: t$_R$ 9.4 min; MS: m/z=400.4 (M+H)$^+$, calculated M$_r$=399.2.

Example 18

Synthesis of D,L-4-nitrophenylalanine methyl ester hydrochloride (22)

SOCl$_2$ (1.27 µl; 18.88 mmol) was added dropwise to an ice-cool solution of (4-nitro)phenylalanine (1 g; 4.72 mmol) in MeOH (5 ml). After 20 h, the solvent was evaporated and the weakly yellow solid was washed with ether and dried.

Yield: 1.19 g (97%); TLC (solvent system F): R$_f$ 0.70; MS: m/z=225.2 (M+H)$^+$, calculated M$_r$=224.1.

Example 19

Synthesis of N-1-adamantyloxycarbonyl-D,L-4-nitrophenylalanine methyl ester (23)

Compound 23 was prepared from compound 22 using Adoc-F as described for compound 10.

Yield: 725 mg (94%); HPLC: t$_R$ 12.7 min; MS: m/z=403.4 (M+H)$^+$, calculated M$_r$=402.2.

Example 20

Synthesis of N-1-adamantyloxylcarbonyl-D,L-4-aminophenylalanine methyl ester (24)

Compound 23 (725 mg; 1.8 mmol) was hydrogenated for 2 h over Pd/C in MeOH (20 ml); the catalyst was subsequently filtered off and the solvent was evaporated. The crude product was chromatographed through silica gel (eluent: n-hexane/AcOEt/AcOH, 49:49:2).

Yield: 556 mg (83%); HPLC: t$_R$ 14.2 min; TLC (solvent system G): R$_f$ 0.54; MS: m/z=373.4 (M+H)$^+$, calculated M$_r$=372.4.

Example 21

Synthesis of N-1-adamantyloxycarbonyl-D,L-4-(N$^\omega$,N$^\omega$-dibenzyloxycarbonyl)guanidinophenylalanine methyl ester (25)

A solution of compound 24 (57 mg; 0.153 mmol), N,N'-dibenzyloxycarbonyl-N"-trifylguanidine (70 mg; 0.153 mmol) and TEA (21 µl; 0.153 mmol) in methylene chloride (500 µl) was stirred at 50° C. for three days in a sealed reaction vessel equipped with a screw closure. The solvent was evaporated and the crude product in AcOEt (10 ml) was washed twice with 5% aqueous KHSO$_4$, water and salt solution. The organic phase was dried (over Na$_2$SO$_4$) and evaporated.

Yield: 96 mg (92%) of a colorless oil; HPLC: t$_R$ 14.5 min; MS: m/z=683.4 (M+H)$^+$, calculated M$_r$=682.3.

Example 22

Synthesis of N-1-adamantyloxycarbonyl-D,L-4-guanidinophenylalanine methyl ester hydrochloride (26)

Compound 26 was obtained by catalytically hydrogenating compound 25 (96 mg; 0.141 mmol) over Pd/C in MeOH (5 ml) which contained 1 M HCl (140 µl; 0.141 mmol). The catalyst was filtered off, the solution was evaporated and the residue was recrystallized from AcOEt/diisopropyl ether.

Yield: 53 mg (83%); HPLC: t$_R$ 9.5 min; MS m/z=415.4 (M+H)$^+$, calculated M$_r$=414.2.

Example 23

Synthesis of N-1-adamantyloxycarbonyl-L-3-amidinophenylalanine methyl ester hydrochloride (27)

Compound 27 was synthesized as described for compound 11, preceding from L-(3-cyano)phenylalanine.

HPLC: t$_R$ 9.6 min; MS: m/z=400.2 (M+H)$^+$, calculated M$_r$=399.2.

Example 24

Synthesis of N-1-adamantyloxycarbonyl-D-3-amidinophenylalanine methyl ester hydrochloride (28)

Compound 28 was synthesized as described for compound 11, proceeding from D-(3-cyano)phenylalanine.

HPLC: t$_R$ 8.2 min; MS: m/z=400.4 (M+H)$^+$, calculated M$_r$=399.2.

Example 25

Synthesis of N-1-adamantyloxycarbonyl-D-3-amidinophenylalanine propylamide hydrochloride (29)

N$^a$-Adoc-D-3-Amidinophenylalanine hydrochloride (50 mg; 0.118 mmol), n-propylamine (29 µl; 0.354 mmol) and HOBT (19 mg; 0.142 mmol) were dissolved in 2 ml of DMF. TBTU (46 mg; 0.142 mmol) was added and the reaction mixture was stirred at room temperature for 3 h. After the solvent had been evaporated off in vacuo, the resulting oil was dissolved in 20 ml of ethyl acetate. The product began to precipitate out immediately and was separated off by centrifugation. The colorless solid was washed with ethyl acetate and dried in vacuo.

Yield: 26 mg (47%); HPLC: $t_R$ 7.8 min; MS: m/z=427.4 (M+H)$^+$, calculated $M_r$=426.3.

Example 26

Synthesis of N-1-adamantyloxycarbonyl-D-3-amidinophenylalanine benzylamide hydrochloride (30)

N$^\alpha$-Adoc-D-3-Amidinophenylalanine hydrochloride (30 mg; 0.071 mmol), benzylamine (23 µl; 0.213 mmol) and HOBT (11 mg; 0.085 mmol) were dissolved in 2 ml of DMF. TBTU (27 mg; 0.085 mmol) was added and the reaction mixture was stirred at room temperature. After 3 h, the precipitated salt was filtered off and the solvent was evaporated in vacuo. The residue was dissolved in 10 ml of ethyl acetate, after which this solution was washed with 5% aqueous NaHCO$_3$ solution and salt solution and dried over anhydrous Na$_2$SO4. After the solvent had been evaporated off in vacuo, the crude product was dissolved in 1 ml of ethyl acetate. 10 µl of 6N HCl in dioxane were added and the product was precipitated with tert-butyl methyl ether. The flocculent precipitate was washed with diethyl ether and dried in vacuo.

Yield: 16 mg (43%); HPLC: $t_R$ 10.3 min; MS: m/z=475.2 (M+H)$^+$, calculated $M_r$=474.3.

Example 27

Synthesis of N-1-adamantyloxycarbonyl-D-3-amidinophenylalanine-(2-phenyl)-1-ethylamine hydrochloride (31)

N$^\alpha$-Adoc-D-3-Amidinophenylalanine hydrochloride (30 mg; 0.071 mmol), phenethylamine (27 µl; 0.213 mmol) and HOBT (11 mg; 0.085 mmol) were dissolved in 2 ml of DMF. TBTU (27 mg; 0.085 mmol) was added and the reaction mixture was stirred at room temperature. After 3 h, the reaction had not come to an end and 15 mg of TBTU (0.047 mmol) were added and the mixture was stirred for a further 3 h. The solvent was evaporated in vacuo. The residue was dissolved in 10 ml of ethyl acetate and this solution was washed three times with 5% aqueous NaHCO$_3$ solution and 1× with 2 ml of 0.5 N HCl and dried over anhydrous Na$_2$SO$_4$. After the solvent had been evaporated off in vacuo, the product was precipitated from iPrOH/DIPE. The flocculent precipitate was washed with diethyl ether and dried in vacuo.

Yield: 10 ml (27%); HPLC: $t_R$ 6.8 min; MS m/z=489.4 (M+H)$^+$, calculated $M_r$=488.3.

Example 27a

Compounds 32 to 36 were synthesized in an analogous manner to the above-described preparation methods.

Compound 32, containing the linker —NH—CO—NH—, inhibits FXa better, by a factor of 3, than does compound 31, containing the linker —O—CO—NH—.

Example 28

Determining the Inhibitor Constants

The measurements were carried out at 25° C. on a microplate reader (MR 5000, Dynatech, Denkendorf, Germany). The test medium consisted of 200 µl of Tris buffer (0.05 M; 0.154 M NaCl, 5% ethanol, pH 8.0), 25 µl of aqueous substrate solution and 50 µl of enzyme solution. Two concentrations of the substrate and five concentrations of the inhibitor were used. Three minutes after adding the enzyme, 25 µl of acetic acid (50%) were added in order to quench the reaction and the optical density was measured at 405 nm. The $K_i$ values were calculated in accordance with Dixon (M. Dixon (1953), Biochem. J. 55, 170–171) using a linear regression. The $K_i$ values given in FIGS. 2 and 3 are means of at least three determinations.

Example 29

Enzymes and Substrates for the $K_i$ Determination

The following enzymes and the corresponding substrates were used at the given final concentrations: bovine thrombin, prepared in accordance with Walsmann (P. Walsmann (1968), Pharmazie 23, 401–402) (2 262 U/mg, final concentration 0.45 U/ml), substrate MeSO$_2$-D-hexahydrotyrosyl-Gly-Arg-pNA (final concentration 0.18 and 0.09 mM); bovine factor X$_a$ (5 U/vial, 0.11 U/ml; Diagnostic Reagents Ltd., Thame, UK), substrate MeSO$_2$-D-Nle-Gly-Arg-pNA (0.36 and 0.18 mM); human factor X$_a$ (0.18 µg/ml; Kordia Lab. Supplies, Leiden, Netherlands), substrate as for bovine factor X$_a$ human plasmin (0.67 CTA U/mg, 0.06 CTA U/ml; Behringwerke AG, Marburg, Germany), substrate Tos-Gly-Pro-Lys-pNA (0.18 and 0.09 mM); human uPA (500 000 U/vial, final concentration 150 U/ml; Ribosepharm GmbH Haan, Germany), substrate Bz-βAla-Gly-Arg-pNA (0.18 and 0.09 mM); bovine pancreas trypsin (42 U/mg, 0.0038 U/ml; Serva, Heidelberg, Germany), substrate MeSO$_2$-D-hexahydrotyrosyl-Gly-Arg-pNA (0.18 and 0.06 mM).

The substrates were supplied by Pentapharm Ltd., Basel, Switzerland.

FIGURES

FIG. 1: Structures and inhibitor strengths of factor X$_a$ inhibitors 1, 2 and 3 from the prior art.

FIG. 2: Derivatives of 3-/4-amidino- or 4-guanidinophenylalanine, respectively, containing N$^\alpha$-substituted carbamate or urea.

FIG. 3: Enantiomerically pure derivatives of 1-adamantyloxycarbonyl-3-amidinophenylalanine methyl ester. $K_i$ values marked with * correspond to $K_i$ values for human factor X$_a$.

FIG. 4: Derivatives of N-1-adamantyloxycarbonyl-3-amidinophenylalanine containing C$^\alpha$-substituted amide. $K_i$ values marked with * correspond to $K_i$ values for human factor X$_a$.

Figure 4A:
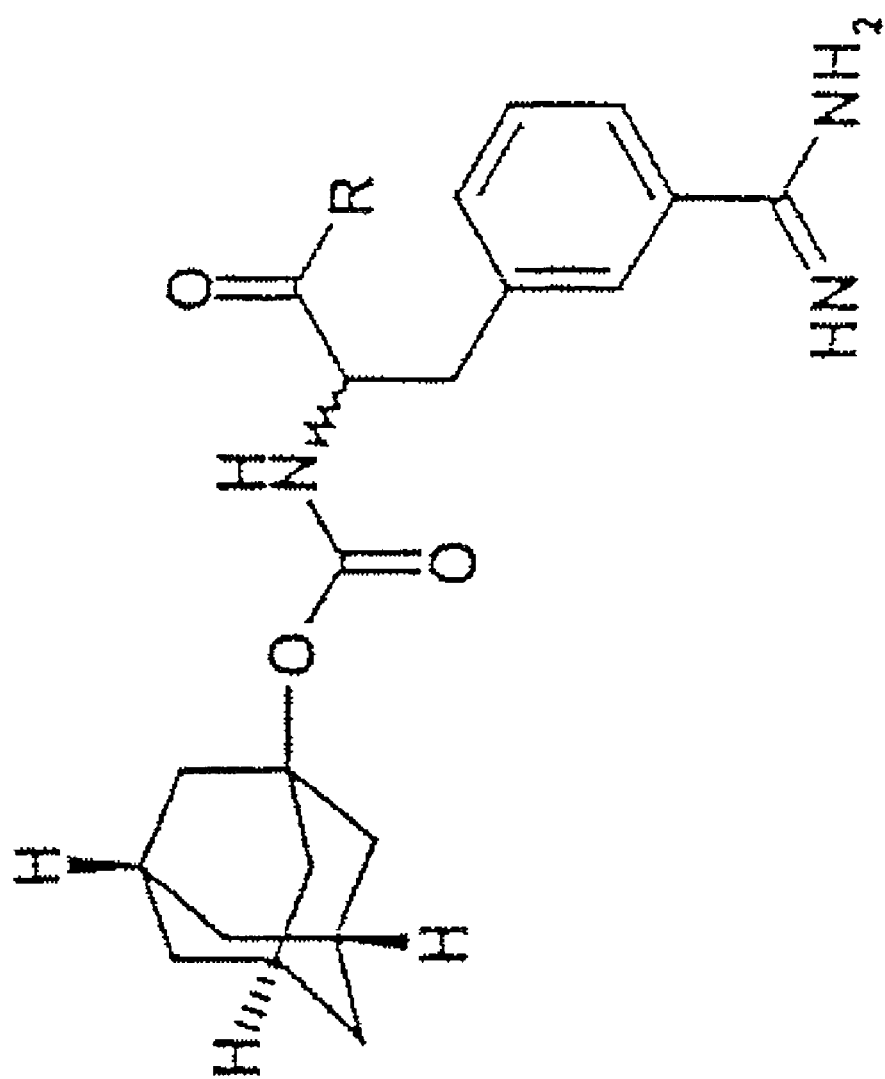

FIG. 4a: Other derivatives of N-1-adamantyloxycarbonylamidinophenylalanine containing C$^\alpha$-substituted amide, with compounds containing different R$^2$ radicals, and their $K_i$ values, being depicted.

Figure 5:
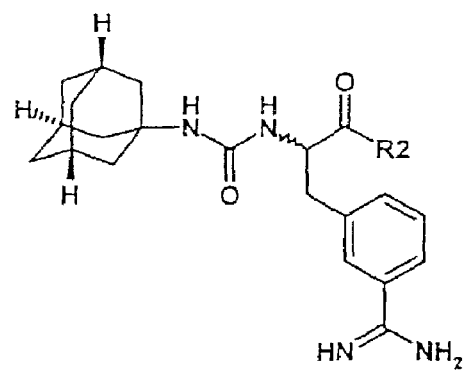

FIG. 5: N-(1-Adamantylaminocarbonyl)-D-3-amidinophenylalanine-(2-phenyl)-1-ethylamide and its $K_i$ values.

The invention claimed is:

1. A compound of structural formula I:

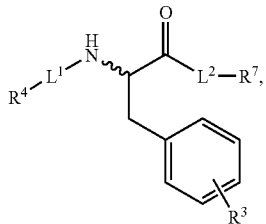

wherein:
- $L^1$ is a linker which is a member selected from the group consisting of —CO—, —CO—NH—, and —COO;
- $R^4$ is t-butyl, phenyl, benzyl, fluorenyl, or adamantyl;
- $L^2$ is a linker which is a member selected from the group consisting of a bond, —$OR^5$—, —NH—$R^5$—, —NH—NH—$R^5$, and —$CH_2$—$R^5$—, wherein $R^5$ is —$(CH_2)_m$— and m is 1 to 3, or $L^2$ is a linker which is NH—$CHR^9$—COO—$(CH_2)_m$ wherein m is 1 to 5 and $R^9$ is a derivatized or underivatized side chain of a natural amino acid;
- $R^7$ is a phenyl, piperidinepyrrol, furan, thiophene, pyridine, naphthalene, anthracene or indole radical which is unsubstituted or is substituted by one or more $R^8$ radicals, wherein $R^8$ is a basic substituent or a substituent functioning as a hydrogen bond donor or acceptor or a halogen; and
- $R^3$ is an amidino, guanidino, amino, alkylamino, aminoalkyl or amide radical and is at the 3 position of the aromatic ring of the phenylalanine radical.

2. The compound of claim 1, wherein $R^8$ is an amidino, guanidino, amino, alkylamino, aminoalkyl, or amide radical.

3. The compound of claim 1, wherein the phenylalanine radical is (R)-chiral.

4. N-1-Adamantyloxycarbonyl-D-3-amidophenylalanine-(2-phenyl)-1-ethylamide.

5. N-1-Adamantyloxycarbonyl-D-3-amidophenylalanine-propylamide.

6. N-1-Adamantyloxycarbonyl-D-3-amidophenylalanine-propylamide benzylamide.

7. The compound of claim 1, in the form of a pharmaceutically acceptable salt.

8. The compound of claim 7, wherein the pharmaceutically acceptable salt is a hydrochloride.

9. A pharmaceutical composition comprising the compound of claim 1 and a pharmaceutically acceptable vehicle.

10. N-1-adamantyloxycarbonyl-D3-amidino-phenylalanine-2-phenyl-1 ethylamide.

* * * * *